United States Patent [19]

Tinney

[11] 4,031,070

[45] June 21, 1977

[54] TETRAPEPTIDES

[75] Inventor: Francis John Tinney, Ann Arbor, Mich.

[73] Assignee: Parke, Davis & Company, Detroit, Mich.

[22] Filed: Mar. 1, 1976

[21] Appl. No.: 662,405

[52] U.S. Cl. .............. 260/112.5 LH; 260/112.5 R; 424/177

[51] Int. Cl.$^2$ ...................... C07C 103/52

[58] Field of Search .......... 260/112.5 R, 112.5 LH

[56] References Cited

UNITED STATES PATENTS 3,725,380   4/1973   Konig et al. ................ 260/112.5 R

OTHER PUBLICATIONS

J. M. Stewart and J. D. Young, "Solid Phase Peptide Synthesis," Freeman and Co., San Francisco, 1969, pp. 9–13.

J. D. Roberts and M. C. Caserio, "Basic Principles of Organic Chemistry," Benjamin Inc., N.Y., 1965, pp. 531, 563–564.

E. Schroder and K. Lubke, "The Peptides," vol. 1, Academic Press, N.Y., 1965, pp. 79–80.

*Primary Examiner*—Delbert R. Phillips
*Attorney, Agent, or Firm*—Stephen Raines; David B. Ehrlinger; George M. Richards

[57] ABSTRACT

New tetrapeptides having the formula A-$R_1$-$R_2$-Ser (benzyl)-Tyr(benzyl)-$R_3$ wherein A is t-butoxycarbonyl, cyclohexylcarbonyl, benzyloxycarbonyl and p-nitrobenzyloxycarbonyl; $R_1$ is L-Trp or L-His(benzyl); $R_2$ is L-Trp or L-His(benzyl); Ser(benzyl) is D-Ser (benzyl) or L-Ser(benzyl); Tyr(benzyl) is D-Tyr(benzyl) or L-Tyr(benzyl); and $R_3$ is lower alkoxy, hydrazino, amino, lower alkylamino or di(lower alkyl) amino.

4 Claims, No Drawings

TETRAPEPTIDES

SUMMARY AND DETAILED DESCRIPTION

The present invention relates to new peptide compounds that are useful as luteinizing hormone releasing factor antagonists and to methods for their production. More particularly, the invention relates to new N-protected tetrapeptides that are represented by the formula

wherein A is t-butoxycarbonyl, cyclohexylcarbonyl, benzyloxycarbonyl or o-nitrobenzyloxycarbonyl; $R_1$ is L-Trp or L-His(benzyl), $R_2$ is L-Trp or L-His(benzyl), Ser(benzyl) is L-Ser(benzyl) or D-Ser(benzyl), Tyr(benzyl) is L-Tyr(benzyl) or D-tyr(benzyl), and $R_3$ is lower alkoxy, hydrazine, amino, lower alkylamino or di(lower alkyl) amino.

In formula I, the conventional symbols for amino acid residues of peptide compounds linked thereto are used and each is intended to have the following meaning: L-Trp, L-tryptophyl; L-His(benzyl), $N^{im}$-benzyl-L-histidyl; L-Ser(benzyl), L-seryl(benzyl); D-Ser(benzyl), D-seryl(benzyl); L-Tyr(benzyl), L-tyrosyl(benzyl); and D-Tyr(benzyl), D-tyrosyl(benzyl). In addition, the term "lower alkyl" is intended to mean a straight, branched or cyclic hydrocarbon moiety of up to 6 carbon atoms, such as methyl, ethyl, isopropyl and cyclopropyl and "lower alkoxy" is intended to mean an alkoxy group having a straight, branched or cyclic hydrocarbon moiety of up to 6 carbon atoms, such as methoxy, ethoxy and isopropoxy. These symbols and terms will also be used in the formulae that follow for other compounds and each such symbol or term should be understood to have the meaning given above.

In accordance with this invention, compounds of the formula I, wherein A, $R_1$ and $R_2$ are as previously defined and $R_3$ is lower alkoxy, are produced by removing a protected tetrapeptide from a resin complex of the following structure

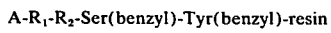   II wherein said resin is a resin employed in solid phase peptide syntheses, such as those disclosed in a text by Stewart and Young, "Solid Phase Peptide Synthesis", W. H. Freeman & Company, San Francisco, 1969, which is incorporated by reference; preferably the resin is a crosslinked copolymer comprising 98 to 99 percent polystyrene crosslinked with 1 to 2 percent divinylbenzene, which is attached to the protected tetrapeptide through a methyleneoxy bridge wherein the methylene group is attached to the polymeric portion of the resin and the oxygen atom is attached to the protected tetrapeptide and A, $R_1$ and $R_2$ are as previously defined; by treating said resin of the formula II with a lower alkyl alcohol in the presence of tertiary amine, such as triethylamine or tripropylamine.

The resin complex is suspended in an excess of the lower alkyl alcohol, preferably methanol for periods of from about 10 hours to 4 days, preferably 16 to 24 hours, at about 15° C. to about 35° C.

While a large excess of the lower alkyl alcohol is preferred, only a catalytic amount of tertiary amine is required; however, larger amounts are preferred, such as about 10 percent volume/volume based on the amount of lower alkyl alcohol employed.

While it is not a preferred procedure, compounds of the formula I wherein $R_3$ is hydrazino, amino, lower alkylamino or di(lower alkyl)amino may be prepared by reacting compounds of the formula II wherein A, $R_1$ and $R_2$ are as previously defined, with dydrazine, ammonia, lower alkylamine or di(lower alkyl)amine.

The resin complex is suspended in a solvent, such as methanol, ethanol, dimethylformamide, etc., at a temperature of from about 0° to 50° C. for periods of from 12 hours to 10 days. When employing less reactive amines, the preferred solvent is dimethylformamide.

The complex resins of the formula II are prepared by coupling a protected amino acid of the formula

   III wherein A and $R_1$ are as previously defined, with a complex resin of the formula

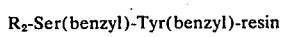   IV in an organic solvent, such as dichloromethane with the aid of dicyclohexylcarbodiimide. The three reactants may be used in about equimolar quantities but excess amounts of the protected amino acid and dicyclohexylcarbodiimide are sometimes advantageous. The reaction is generally conducted at about room temperature for a period of from about 15 minutes to about 16 hours.

The complex resins of the formula IV are prepared by treating complex resins of the formula

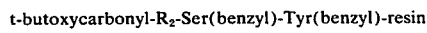   V with a large excess of trifluoroacetic acid utilizing dichloromethane as the solvent at temperatures of from 20° to 30° C. for about 10 minutes, followed by liberation of the amine from its trifluoroacetic acid salt by addition of a base such as triethylamine.

The complex resins of formula V are prepared by coupling

to complex resins of the formula

   VI using the reaction procedure described for the preparation of compounds of the formula II.

The complex resins of the formula VI are prepared by treating the complex resins of the formula

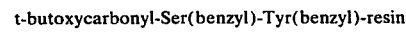   VII with trifluoroacetic acid using the reaction procedure for the preparation of compounds of the formula IV.

The complex resins of the formula VII are prepared by coupling

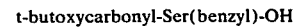

to the complex resins of the formula

   VIII according to the procedure used for the preparation of compounds of formula II.

The complex resins of the formula VIII are prepared by treating the complex resins of the formula t-butoxycarbonyl-Tyr(benzyl)-resin with trifluoroacetic acid using the reaction procedure for the preparation of compounds of the formula IV.

In accordance with this invention, compounds of the formula I, wherein A, $R_1$ and $R_2$ are as previously described and $R_3$ is hydrazino, amino, lower alkylamino or di(lower alkyl)amino are prepared by reacting a compound of the formula I wherein $R_3$ is alkoxy, preferably methoxy, with hydrazine, ammonia, lower alkylamine or di(lower alkylamine).

The reactions are conducted at temperatures of from about 5° to 100° C. for from 3 hours to 4 days, preferably about room temperature. Generally, a large excess of hydrazine, preferably used in the form of its hydrate, or amine is used (over five fold). The reaction is usually carried out in a non-reactive solvent, such as a lower alkyl alcohol, preferably methanol or ethanol, an ether such as tetrahydrofuran or dioxane, dimethylformamide or mixtures thereof.

In addition, in accordance with this invention, compounds of the formula I, wherein A, $R_1$ and $R_2$ are as previously defined and $R_3$ is amino, lower alkylamino or di(lower alkyl)amino are prepared by reacting a compound of the formula A-$R_1$-$R_2$-Ser(benzyl)-Tyr(benzyl)-$N_3$    IX with ammonia, lower alkylamine or di(lower alkyl)amine in a non-reactive solvent such as dimethylformamide, dioxane, tetrahydrofuran or mixtures thereof. The reaction is carried out at about −30° C. to about 0° C. for about 12 to 24 hours, preferably −20° C. to 0° C. for from 16 to 19 hours. The two reactants are used in approximately equimolar amounts although a slight excess of the amine, about 10 percent, is preferred. When A is t-butoxycarbonyl, care should be taken to avoid the presence of a large excess of acid.

The azide compounds of the formula IX are normally prepared in situ by reacting a peptide hydrazide compound of the formula I wherein A, $R_1$ and $R_2$ are as previously defined and $R_3$ is hydrazino, with a lower alkyl nitrite, preferably isoamyl nitrite in the presence of an acid, preferably hydrochloric acid, in an inert solvent medium such as dimethylformamide, and the resultant azide is reacted further as described above without isolation. The preferred acid for use in the azide preparation is a solution of hydrogen chloride in dimethylformamide or tetrahydrofuran; between 3 and 6 equivalents of acid are used for each equivalent of the hydrazide of formula I. The preparation of the azide is carried out at a temperature between −30° C. and 0° C.

Following the in situ formation of the azide of formula IX and prior to the further reaction of the peptide azide with the appropriate amine to form certain tetrapeptides of formula I, a tertiary amine such as triethylamine is added to the reaction mixture to neutralize the acid used.

Compounds of the formula I wherein A, $R_1$ and $R_2$ are as previously described and $R_3$ is hydrazino, amino, lower alkylamino or di(lower alkyl)amino are prepared by coupling a compound of the formula A-$R_1$-$R_2$-Ser(benzyl)-Tyr(benzyl)-OH    X with hydrazine, ammonia, lower alkylamine or di(lower alkyl)amine in an inert solvent in the presence of dicyclohexylcarbodiimide.

The above reaction is carried out using approximately equivalent amounts of reactants in a solvent such as dichloromethane, chloroform, tetrahydrofuran, dioxane or dimethylformamide, or mixtures thereof. The preferred solvent is tetrahydrofuran.

The temperature range for carrying out the reaction may be from 5° to 50° C., preferably room temperature for periods of from 10 hours to 5 days.

1-Hydroxybenzotriazole may also be used in the above reaction in addition to the dicyclohexylcarbodiimide. The 1-hydroxybenzotriazole is added in a ratio of one to two equivalents when compared to the reactants.

The compounds of the formula X are prepared by the hydrolysis of a compound of formula I wherein A is as previously defined and $R_3$ is lower alkoxy. The reaction is conducted at temperatures of from 20° C. to 30° C. using about 0.5 ml. of the two normal aqueous sodium hydroxide solution and 10 ml. of solvent, usually water or an alcohol such as methanol, for each millimole of ester. The compound of formula X is isolated after acidification with aqueous citric acid.

The compounds of this invention can exist in anhydrous forms as well as in solvated, including hydrated, forms. In general, the hydrated forms and the solvated forms with pharmaceutically-acceptable solvents are equivalent to the anhydrous or unsolvated form for the purposes of the invention.

Tetrapeptides of this invention were screened for LRF antagonist activity in vitro using rat anterior pituitary cell cultures as described by Vale et al. [Endocrinology, 91, 562 (1972)]. The inhibition of LRF (luteinizing hormone release factor) induced luteinizing hormone (LH) release into the culture medium is the endpoint in this in vitro bioassay.

Following are the results of the above tests on certain preferred compounds.

| ACTIVITY TABLE FOR IN VITRO TEST IN RAT ANTERIOR PITUITARY CELL CULTURES | | | |
|---|---|---|---|
| | Molar Conc. | LH Value ng/ml. | % LH Release Inhibition |
| $N^\alpha$-t-butoxycarbonyl-L-tryptophyl-$N^{im}$-benzyl-L-histidyl-O-benzyl-L-seryl-O-benzyl-L-tyrosine N-ethylamide | $1 \times 10^{-6}$ | 19.19 | 81 |
| LRF Control | $3.5 \times 10^{-10}$ | 49.99 | |
| Saline Control | | 11.75 | |
| $N^\alpha$-t-butoxycarbonyl-$N^{im}$-benzyl-L-histidyl-L-tryptophyl-O-benzyl-L-seryl-O-benzyl-L-tyrosine N-ethylamide | $1 \times 10^{-6}$ | 22.16 | 73 |
| LRF Control | $3.5 \times 10^{-10}$ | 49.99 | |

ACTIVITY TABLE FOR IN VITRO TEST IN RAT ANTERIOR PITUITARY CELL CULTURES
-continued

| | Molar Conc. | LH Value ng/ml. | % LH Release Inhibition |
|---|---|---|---|
| Saline Control | | 11.75 | |
| $N^\alpha$-t-butoxycarbonyl-L-tryptophyl-$N^{im}$-benzyl-L-histidyl-O-benzyl-L-seryl-O-benzyl-L-tyrosine methyl ester | $1 \times 10^{-6}$ | 21.20 | 54 |
| LRF Control | $2.5 \times 10^{-10}$ | 38.98 | |
| Saline Control | | 6.25 | |

The luteinizing hormone releasing factor is known to be formed in the hypothalamus of mammals, from which it is released and transported by way of the hypothalamic hypophyseal portal system to the anterior pituitary, where is stimulates the secretion of luteinizing hormone. The secretion of luteinizing hormone from the anterior pituitary in turn is known to effect ovulation in experimental animals. Thus, LRF can be used to induce ovulation in animals. For a report of the structure of LRF, which has also been referred to as luteinizing hormone releasing hormone, or LH-RH, and its biological activity, see *Science*, Vol. 174, No. 4008, Oct. 29, 1971, pages 511–412. Thus, the tetrapeptides of this invention are useful in controlling ovulation and in restricting fertility. The invention is illustrated by the following examples.

EXAMPLE 1

$N^\alpha$-t-Butoxycarbonyl-L-tryptophly-$N^{im}$-benzyl-L-histidyl-O-benzyl-L-seryl-O-benzyl-L-tyrosine methyl ester A mixture of 50 g. of chloromethylated polystyrene resin having 1.16 mmole of chlorine per gram, and 36 g. of $N^\alpha$-t-butoxycarbonyl-L-tyrosine in one liter of ethanol is treated with 9.8 g. of triethylamine and refluxed for 3 days. The resin is separated by filtration, washed with ethanol, water, methanol, dichloromethane and ether, successively, and then dried overnight at 40° C. giving the t-butoxycarbonyl-O-benzyl-L-tyrosine resin.

A tubular flask of 400 ml. capacity, having a sintered glass disc and stopcock at one end and a suitably placed opening for addition of materials at the other is clamped to a motor which imparts a rocking motion to the flask. The flask is charged with 3.8 g. of $N^\alpha$-t-butoxycarbonyl-O-benzyl-L-tyrosine resin and 200 ml. of dichloromethane and agitated for one-half hour. The liquid is then drained from the flask by connecting a suction, through a trap, to the stopcock. The resin is retained in the flask by means of the sintered glass disc. The $N^\alpha$-t-butoxycarbonyl protecting group is removed by rocking the resin with 100 ml. of trifluoroacetic acid and 100 ml. of dichloromethane for ten minutes. The liquid is drained from the flask and the trifluoroacetate salt of O-benzyl-L-tyrosine resin is washed five times with 200 ml. of dichloromethane each time. The trifluoroacetate salt of the O-benzyl-L-tyrosine resin is converted to O-benzyl-L-tyrosine resin by the addition of 20 ml. of triethylamine in 200 ml. of cold dichloromethane and rocking the reaction for ten minutes. The flask is drained and the resin again washed five times with 200 ml. of dichloromethane each time. The O-benzyl-L-serine moiety is coupled to the O-benzyl-L-tyrosine resin by adding 1.5 g. 4.5 mmol, of $N^\alpha$-t-butoxycarbonyl-O-benzyl-L-serine in 200 ml. of dichloromethane, shaking for sixty minutes, adding 1.1 g., 4.5 mmol, of dicyclohexylcarbodiimide in 50 ml. of dichloromethane and rocking the reaction flask for 20 hours. The flask is drained and the resin washed three times with 250 ml. of dichloromethane each time. Trifluoroacetic acid (100 ml.) and dichloromethane (100 ml.) are used as above to remove the t-butoxycarbonyl protecting group and the resin drained and washed as before. Triethylamine, 20 ml. in 200 ml. of cold dichloromethane, is used to liberate the O-benzyl-L-seryl-O-benzyl-L-tyrosine resin, which is treated with 1.7 g., 5 mmol, of $N^\alpha$-t-butoxycarbonyl-$N^{im}$-benzyl-L-histidine in 200 ml. of dichloromethane, rocked for thirty minutes and 1.1 g. of dicyclohexylcarbodiimide added in 50 ml. of dichloromethane. The coupling reaction is rocked for 20 hours, the flask drained and the resin washed three times with 250 ml. of dichloromethane each time. Trifluoroacetic acid (100 ml.) and dichloromethane (100 ml.) are used as above to remove the t-butoxycarbonyl protecting group and the resin drained and washed as before. Triethylamine, 20 ml. in 200 ml. of cold dichloromethane, is used to liberate the $N^{im}$-benzyl-L-histicyl-O-benzyl-L-seryl-O-benzyl-L-tyrosine resin, which is treated with 1.5 g., 5 mmol, of $N^\alpha$-t-butoxycarbonyl-L-tryptophan in 200 ml. of dichloromethane, rocked for thirty minutes and 1.1 g. of dicyclohexylcarbodiimide added in 50 ml. of dichloromethane. The coupling reaction is rocked for twenty hours, the flask drained and the resin washed two times with 200 ml. of dichloromethane each time. The resin is then washed from the flask with methanol-chloroform (1:2), three times with 200 ml., and washed further three times with 200 ml. of methanol and three times with 200 ml. of ether. It is then air-dried for 2 hours; 4.7 g.

The dried resin is stirred for 2 days at room temperature with 200 ml. of methanol and 20 ml. of triethylamine, filtered and the filtrate evaporated. The crude product is an oil which is chromatographed on silica gel with 20% methanol in chloroform to yield 1.6 g. of $N^\alpha$-t-butoxycarbonyl-L-tryptophyl-$N^{im}$-benzyl-L-histidyl-O-benzyl-L-seryl-O-benzyl-L-tyrosine methyl ester as a hemi-hydrate, m.p. 87°–91° C.

EXAMPLE 2

$N^\alpha$-t-Butoxycarbonyl-L-tryptophyl-$N^{im}$-benzyl-L-histidyl-O-benzyl-L-seryl-O-benzyl-L-tyrosine N-ethylamide The methyl ester of Example 1, 0.3 g., is mixed in 100 ml. of methanol and 5 ml. of ethylamine at room temperature for 2 days. After removal of the methanol and ethylamine the crude product is chromatographed on silica gel with chloroform-methanol-water (60:30:5) to give 0.22 g.; m.p. 93°–99° C.

EXAMPLE 3

$N^\alpha$-t-Butoxycarbonyl-$N^{im}$-benzyl-L-histidyl-L-tryptophyl-O-benzyl-L-seryl-O-benzyl-L-tyrosine methyl ester $N^\alpha$-t-Butoxycarbonyl-$N^{im}$-benzyl-L-histidyl-L-tryptophyl-O-benzyl-L-seryl-O-benzyl-L-tyrosine resin is prepared according to the procedure of Example 1 from $N^\alpha$-t-butoxycarbonyl-O-benzyl-L-tyrosine resin, 10 g., 7 mmol, by reacting successively with (1) 3.2 g., 11 mmol, of $N^\alpha$-t-butoxycarbonyl-O-benzyl-L-serine and 2.3 g., 11 mmol, of dicyclohexylcarbodiimide, (2) 3.3 g., 11 mmol. of $N^\alpha$-t-butoxycarbonyl-L-tryptophan and 2.3 g. of dicyclohexylcarbodiimide and (3) 3.8 g., 11 mmol, of $N^\alpha$-t-butoxycarbonyl-$N^{im}$-benzyl-L-histidine and 2.3 g. of dicyclohexylcarbodiimide.

The resin thus obtained, 12.7 g., is stirred in 200 ml. of methanol and 20 ml. of triethylamine of two days at room temperature. After filtration and evaporation the crude N -t-butoxycarbonyl-$N^{im}$-benzyl-L-histidyl-L-tryptophyl-O-benzyl-L-seryl-O-benzyl-L-tyrosine methyl ester is chromatographed on silica gel with 20% methanol in benzene to yield 4.7 g.; m.p. 77°–81° C.

EXAMPLE 4

$N^\alpha$-t-Butoxycarbonyl-$N^{im}$-benzyl-L-histidyl-L-tryptophyl-O-benzyl-L-seryl-O-benzyl-L-tyrosine N-ethylamide $N^\alpha$-t-Butoxycarbonyl-$N^{im}$-benzyl-L-histidyl-L-tryptophyl-O-benzyl-L-seryl-O-benzyl-L-tyrosine methyl ester, 0.4 g., is mixed in 100 ml. of methanol and 5 ml. of ethylamine at room temperature for two days. After removal of the methanol and ethylamine the crude product is chromatographed on silica gel with chloroform-methanol-water (60:30:5) to yield 0.3 g.; m.p. 120°–125° C.

I claim:

1. A tetrapeptide represented by the formula $$A-R_1-R_2-Ser(benzyl)-Tyr(benzyl)-R_3$$

wherein A is t-butoxycarbonyl, cyclohexylcarbonyl, benzyloxycarbonyl or p-nitrobenzyloxycarbonyl; $R_1$ is L-Trp or L-His(benzyl), $R_2$ is L-Trp or L-His(benzyl), Ser(benzyl) is L-Ser(benzyl) or D-Ser(benzyl), Tyr(benzyl) is L-Tyr(benzyl) or D-Tyr(benzyl), and $R_3$ is lower alkoxy, hydrazino, amino, lower alkylamino or di(lower alkyl)amino.

2. The compound of claim 1 having the name $N^\alpha$-t-butoxycarbonyl-L-tryptophyl-$N^{im}$-benzyl-L-histidyl-O-benzyl-L-seryl-O-benzyl-L-tyrosine methyl ester.

3. The compound of claim 1 having the name $N^\alpha$-t-butoxycarbonyl-L-tryptophyl-$N^{im}$-benzyl-L-histidyl-O-benzyl-L-seryl-O-benzyl-L-tyrosine N-ethylamide.

4. The compound of claim 1 having the name $N^\alpha$-t-butoxycarbonyl-$N^{im}$-benzyl-L-histidyl-L-tryptophyl-O-benzyl-L-seryl-O-benzyl-L-tyrosine N-ethylamide.

* * * * *